United States Patent [19]
Mueller et al.

[11] Patent Number: 5,738,680
[45] Date of Patent: Apr. 14, 1998

[54] LASER DEVICE WITH PIERCING TIP FOR TRANSMYOCARDIAL REVASCULARIZATION PROCEDURES

[75] Inventors: Richard L. Mueller, Byron; Stuart D. Harman, San Jose, both of Calif.

[73] Assignee: Eclipse Surgical Technologies, Inc., Sunnyvale, Calif.

[21] Appl. No.: 628,849

[22] Filed: Apr. 5, 1996

[51] Int. Cl.⁶ ................................................. A61B 17/36
[52] U.S. Cl. ............................. 606/15; 606/7; 607/89
[58] Field of Search .................... 607/89; 606/7, 606/10, 13–16

[56] References Cited

U.S. PATENT DOCUMENTS

| | | | |
|---|---|---|---|
| 4,658,817 | 4/1987 | Hardy | 606/7 |
| 4,846,171 | 7/1989 | Kauphusman et al. | 606/16 |
| 5,554,152 | 9/1996 | Aita et al. | 606/7 |

FOREIGN PATENT DOCUMENTS

| | | |
|---|---|---|
| 0515867 A2 | 2/1992 | European Pat. Off. . |
| WO 94/14383 A1 | 7/1994 | WIPO . |
| WO 95/17127 A1 | 6/1995 | WIPO . |

*Primary Examiner*—Ruth S. Smith
*Attorney, Agent, or Firm*—Janet Kaiser Castaneda; Christopher N. Sears; Roger W. Erickson

[57] ABSTRACT

The method for combined mechanical/laser myocardial revascularization of a human heart includes: inserting a mechanical piercing device and an elongated flexible lasing apparatus into the chest cavity of a patient; mechanically piercing, micro-tearing or spreading the epicardium of the heart; and then lasing from beneath the epicardium through the myocardium. The apparatus is guided to an area exterior to a ventricle of the patient's heart, and the distal end of the optical fiber apparatus is placed internal to the exterior wall of the heart through an opening which has been created by mechanically piercing, micro-tearing or spreading the epicardium, so that the myocardium and not the epicardium is irradiated with laser energy to allow passage of said optical fiber distal end or said laser energy into the left ventricular cavity without causing a laser irradiation of the epicardium which might be a cause of operative bleeding and for better allowing the sealing of the epicardium after the apparatus is removed. The apparatus includes a hand-held device controllable by the surgeon having a removable distal head end with a replaceable piercing member and utilizing a vacuum source to provide a suction force at the head end.

21 Claims, 5 Drawing Sheets

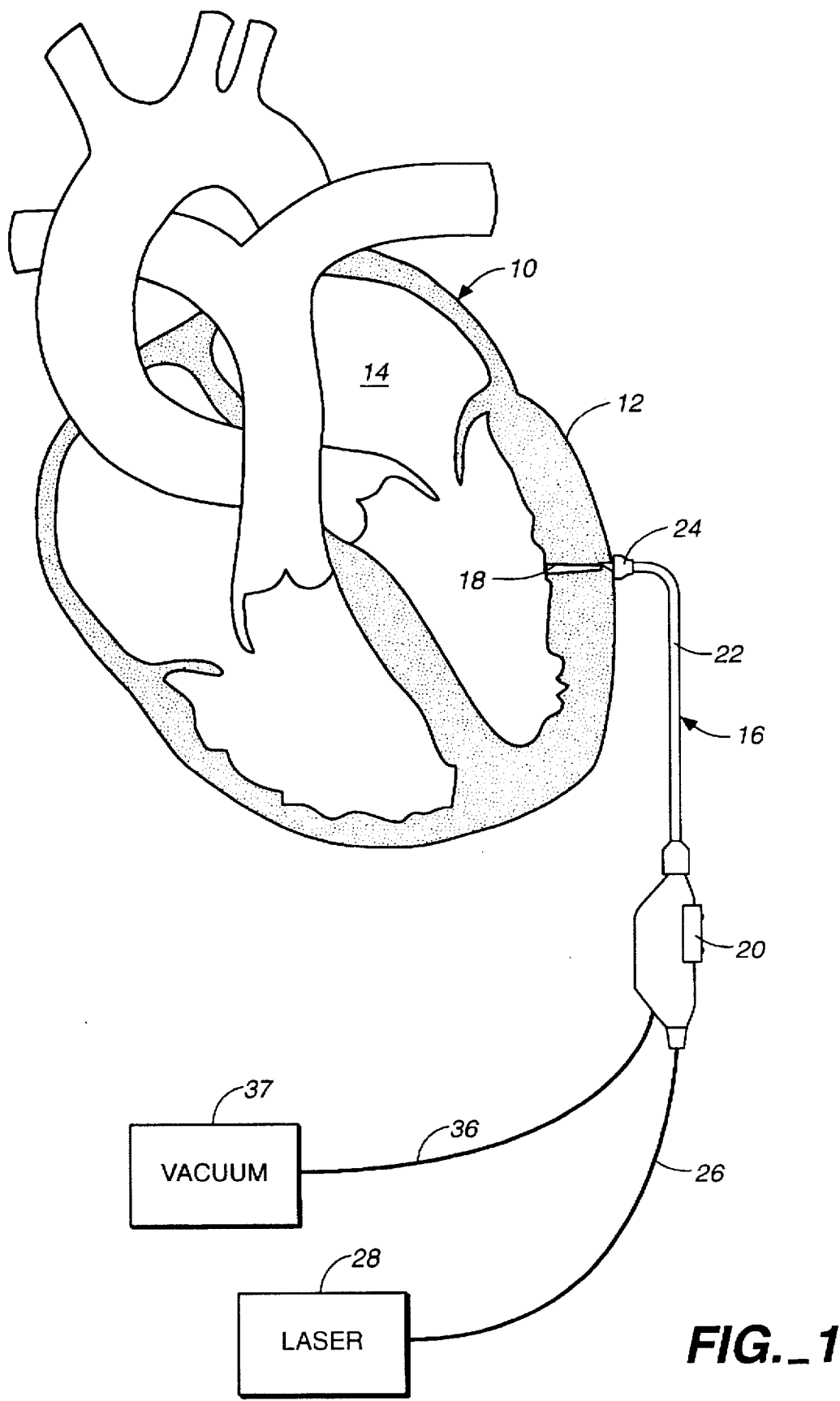
FIG._1

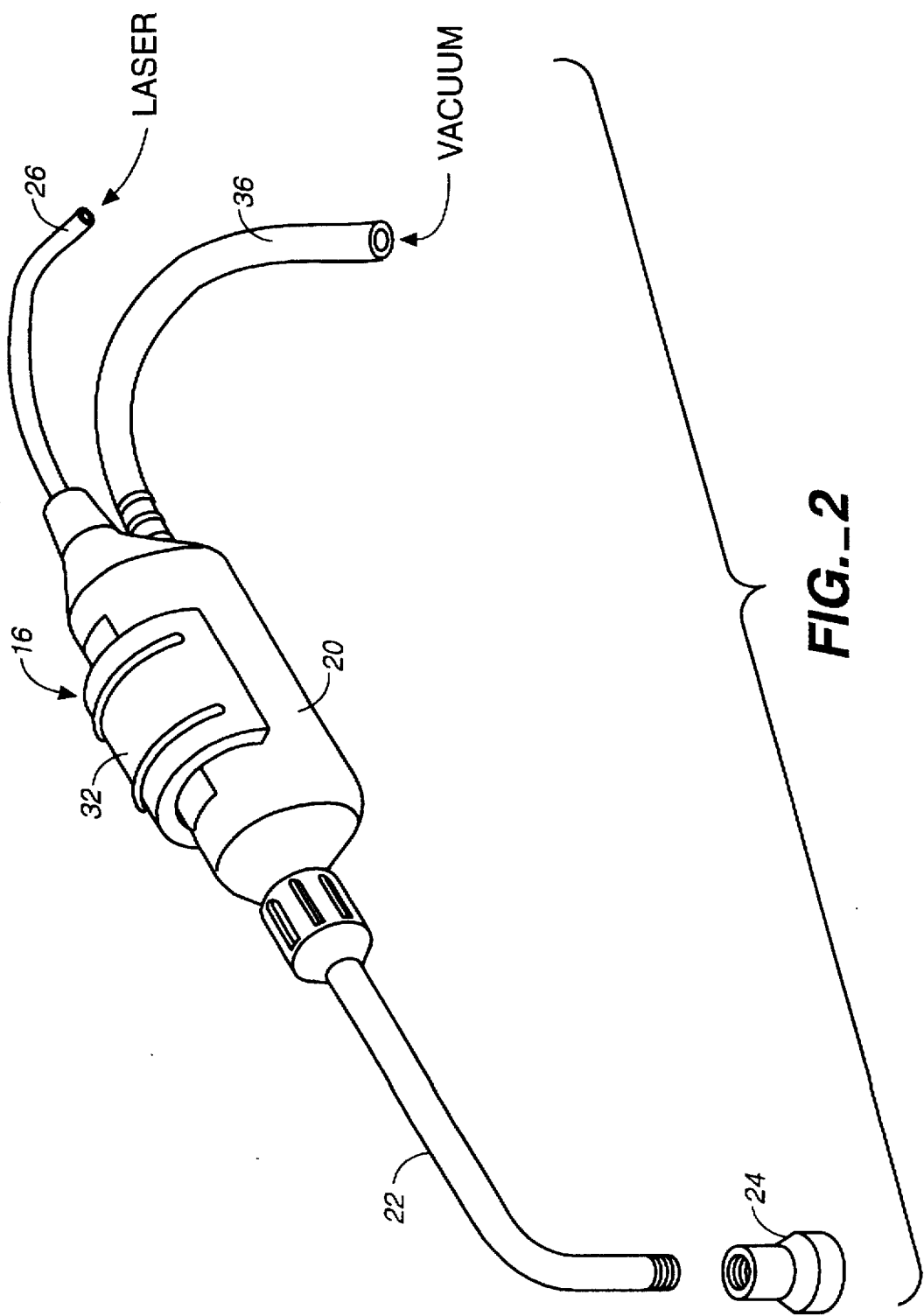

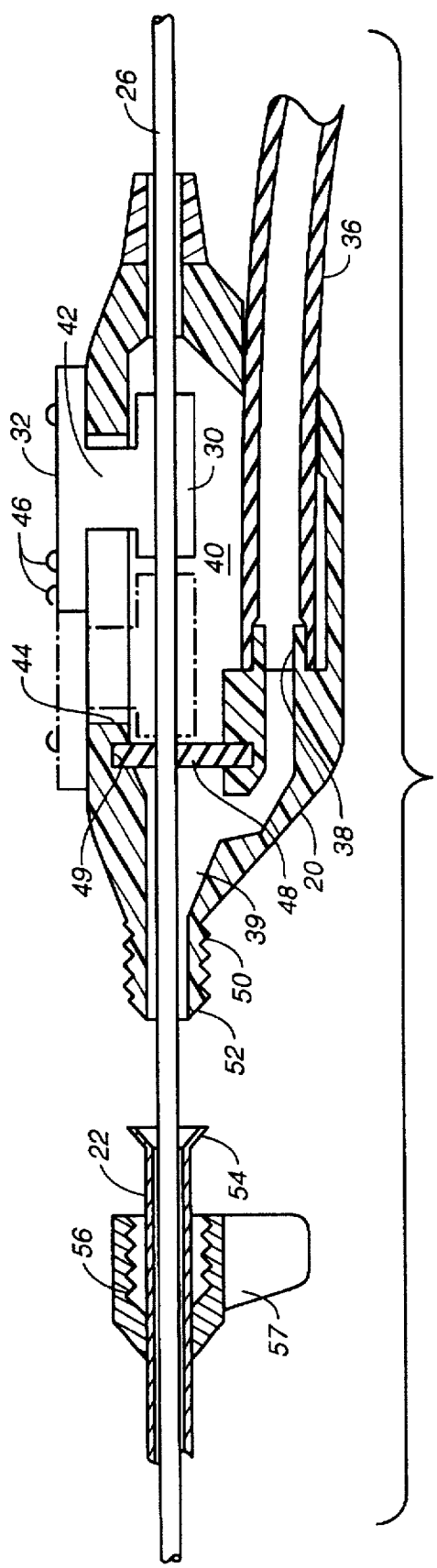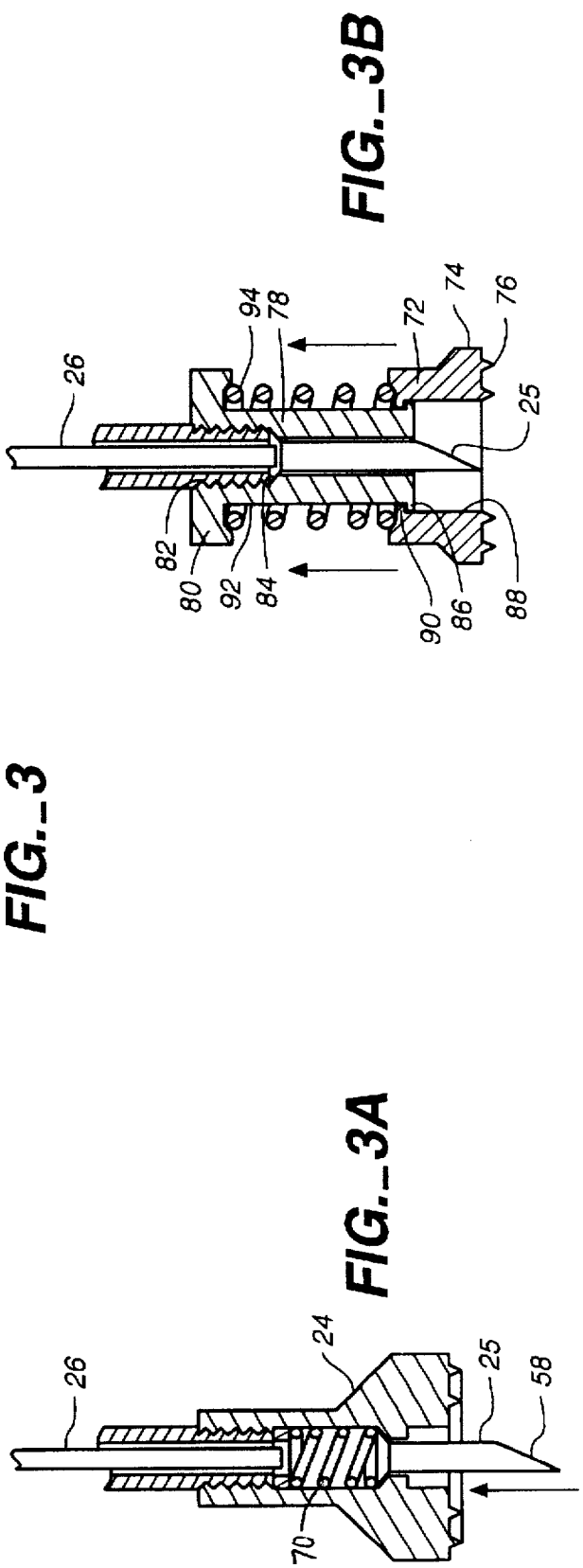
FIG._3
FIG._3B
FIG._3A

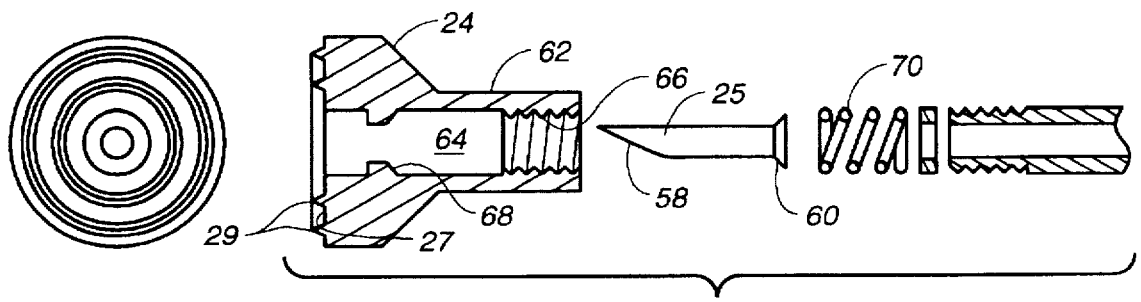
FIG._4     FIG._5
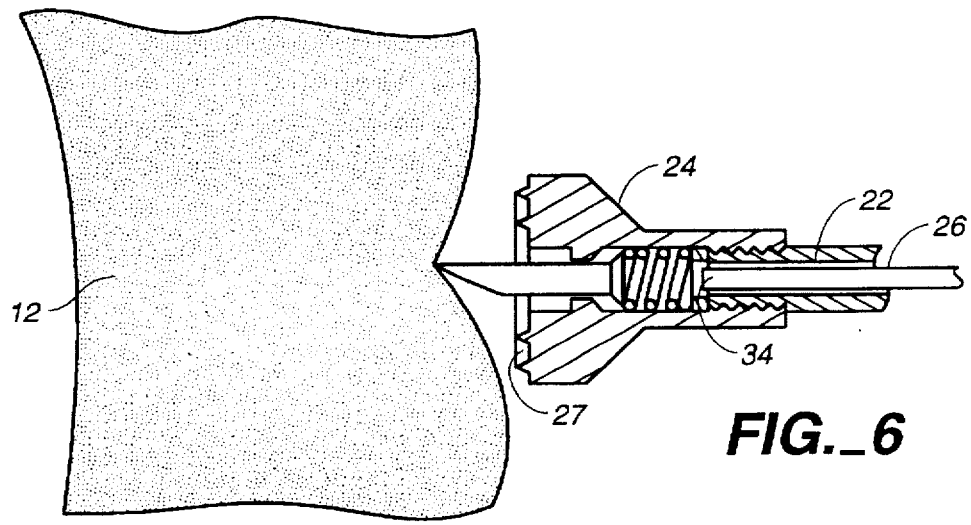
FIG._6
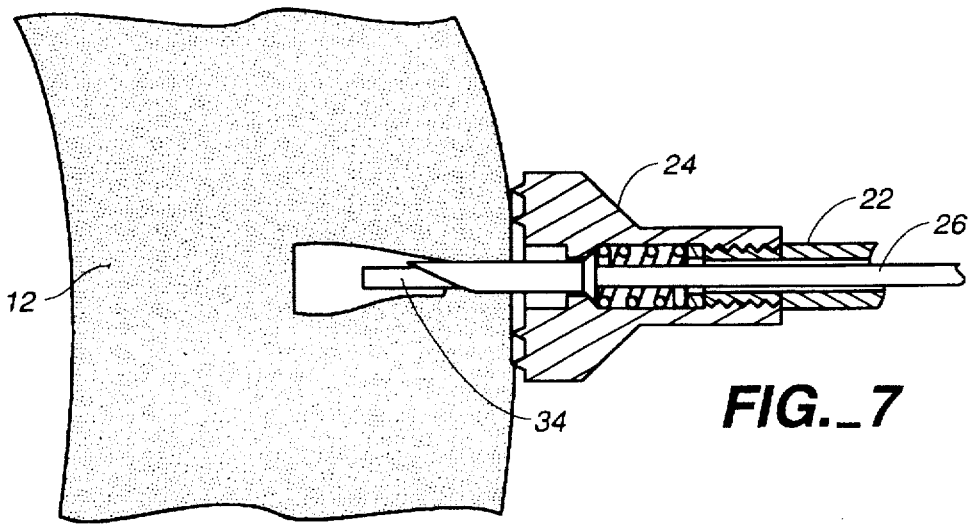
FIG._7

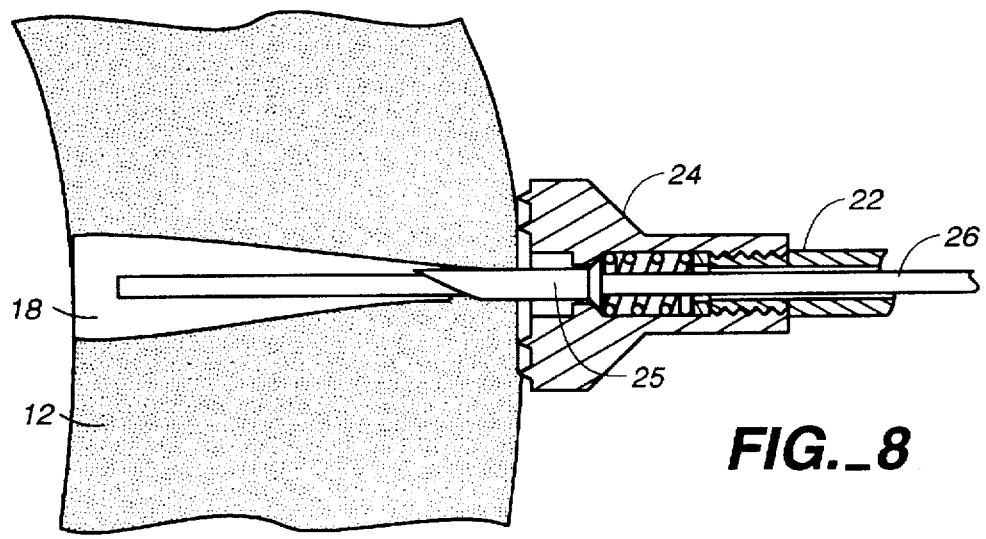
FIG._8
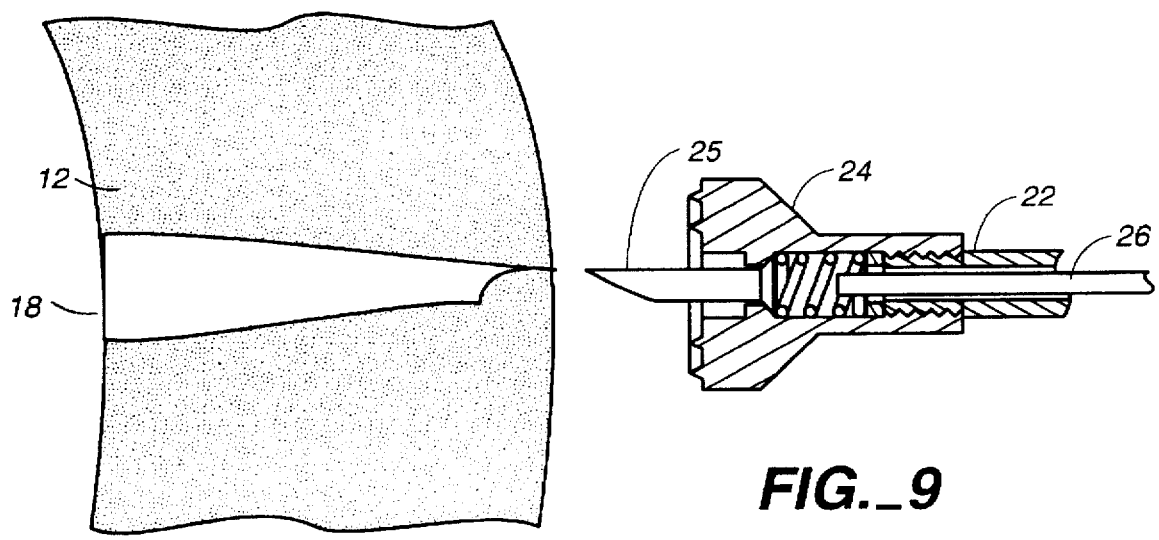
FIG._9

LASER DEVICE WITH PIERCING TIP FOR TRANSMYOCARDIAL REVASCULARIZATION PROCEDURES

FIELD OF INVENTION

This invention relates to the field of laser surgery, and more particularly to an improved laser surgery device for use in procedures for increasing the flow of blood to heart muscle.

BACKGROUND OF THE INVENTION

Medical science has developed a wide variety of methods for counteracting the effects of cardiovascular disease including open heart and by-pass surgery. Non-surgical procedures such as percutaneous transliminal coronary angioplasty, laser angioplasty, and atherectomy have also been developed.

One alternative to the aforementioned procedures is known as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. The resultant channel through the myocardium was funnel-like. A problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al U.S. Pat. No. 5,380,316. Aita, commenting on the Hardy needle device, contends that mechanical piercing was undesirable because it entailed some degree of tearing of the pierced tissue, and that tearing often leads to fibrosis as the mechanical tear heals, a factor that severely diminishes the effectiveness of the TMR treatment. Aita, et al also contends that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini TMR procedure with respect to the aforementioned bleeding problem in the outer surface of the epicardium.

In a copending application Ser. No. 08/607,782, allowed, which is assigned to the assignee of the present application, an improved apparatus and method for TMR procedures is disclosed. In this application the epicardium membrane of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed the opening that was made mechanically in the epicardium tends to close to prevent excessive bleeding from the channel formed in the myocardium.

Under certain operating conditions, the characteristics of the epicardium membrane may vary so the physician may elect to use one or more different tip members on the hand-held device for carrying out the aforesaid improved TMR procedure. Also, it is desirable that the physician be able to pierce the epicardium in the most efficient manner and thereby minimize the size of the opening necessary to accommodate the advancing fiber element. The improved TMR device of the present invention solves these problems.

It is therefore a general object of the present invention to provide an improved apparatus for performing laser myocardial revascularization that solves the problems of the aforementioned prior devices and procedures.

A further object of the present invention is to provide a less invasive and safer apparatus for performing laser myocardial revascularization which does not diminish the effectiveness of the TMR treatment and eliminates the problem of excessive bleeding from the patient's epicardium following the channel forming procedure.

It is a further object of the present invention to provide an apparatus for performing laser myocardial revascularization which utilizes mechanical perforation or piercing of heart tissue to promote sealing of the epicardium but in such a way as to minimize the effect of any fibrosis which such perforation may cause, thereby maintaining the effectiveness of the TMR procedure.

It is a further object of the present invention to provide an improved device for performing a TMR that procedure facilitates the use of interchangeable and/or disposable distal tips on a hand held device for making an initial epicardium opening so that the device can thereafter advance the distal end of a laser emitting fiber element through the patient's myocardium.

Still another object of the present invention is to provide an improved device for performing a TMR procedure wherein a cone-shaped channel is formed whose wider end is at the endocardium and whose narrow end is closed beneath the epicardium to promote blood perfusion from the left ventricular cavity to avoid epicardial bleeding.

Yet another object of the invention is to provide a device for use in a TMR procedure which uses air suction during its operation to draw blood into the channel just formed and thereby enhance the effectiveness of the procedure.

SUMMARY OF THE INVENTION

The present invention comprises a method and apparatus for combined mechanical/laser myocardial revascularization of a human heart that fulfills the aforesaid objectives. A hand-held device which includes a mechanical piercing element for making an initial opening in the epicardium membrane of the heart combined with an elongated flexible lasing apparatus including an optical fiber bundle is inserted into the chest cavity of a patient. In one form, the device includes a detachable distal tip assembly including a hollow piercing means that mechanically penetrates, micro-tears or spreads the epicardium muscle fibers of the heart. The tip assembly includes a circular flange that forms a stop member with a face for engaging the epicardium outer surface and a body portion that retains the hollow piercing member. The latter may be biased by a spring to provide a desired piercing characteristic. Within this hollow piercing member is the distal end of the optical fiber bundle. After the piercing member penetrates the epicardium of the exterior wall of the heart, laser energy is emitted from the distal end of the optical fiber bundle as it is advanced by the surgeon beyond the piercing member using a control knob on the handle of the operating device. Thus, the myocardium and not the epicardium is irradiated with laser energy from said optical fiber distal end to form a channel as it moves into the left ventricular chamber without doing any laser irradiation of the epicardium which could cause operative bleeding. As the fiber element moves through the myocardium, an air suction conduit connected to the tip assembly provides a means for cleaning debris from the channel being formed and also keeping the outer surface of the epicardium firmly against the stop member of the tip assembly. Sealing of the epicardium occurs after the piercing member of the device is removed so that a minimum of bleeding occurs after each TMR procedure. With the present device, the laser energy disbursed through the myocardium as a noncollimated, expanding beam creates a wider channel at the exit of the channel into the left ventricular cavity than within the myocardium so that revascularization can take place in the most effective manner.

Other objects, advantages and features of the present invention will be apparent to those skilled in the art from the following detailed description and the accompanying drawings.

DETAILED DESCRIPTION OF DRAWING

FIG. 1 is a schematic view in section of a human heart showing revascularization of the myocardium utilizing a device according to the present invention.

FIG. 2 is an enlarged view in perspective showing a device embodying principles of the invention for implementing the revascularization procedure of FIG. 1.

FIG. 3 is an enlarged exploded and fragmentary view in section of the device shown in FIG. 2 showing details of the handle portion and the advancing mechanism for linear movement of the movable fiber element.

FIG. 3A is a fragmentary view in section of the distal end member for the device shown in FIG. 3.

FIG. 3B is a view in section showing an alternate form of the distal end member according to the invention.

FIG. 4 is an end view of the distal end member of the device of FIG. 3A.

FIG. 5 is an exploded view in elevation and in section of the distal end member for the device of FIG. 2.

FIGS. 6–9 are enlarged views in elevation and in section showing the end member of FIG. 3A assembled and in operation during a typical TMR procedure according to the invention.

DETAILED DESCRIPTION OF EMBODIMENT

With reference to the drawings, FIG. 1 diagrammatically depicts a human heart 10 with the epicardium 12 of the left ventricle 14 exposed where a Trans-Myocardial Revascularization (TMR) procedure according to the invention is to be performed. Preliminary to the procedure the surgeon makes an incision in the patient's chest to expose the outer wall (epicardium) of the heart's left ventricle. In a human heart the wall of the left ventricle, is comprised of an outer layer, the epicardium, the main muscle thickness, the myocardium, and the inner layer or endocardium. The epicardium is comprised of a smooth, moist serous membrane which is somewhat tougher than the other tissue layers of the heart muscle.

In carrying out the method of the present invention, the surgeon utilizes a hand-held device 16 which is manipulated and operated to form a series of revascularization channels 18 in the myocardium of the patient's heart at selected spaced apart locations.

In accordance with the principles of the invention, each of channels is formed by first piercing the epicardium membrane to form a relatively small opening through which the distal end of an optical fiber bundle can be forced to engage the myocardium. The fiber bundle is connected to a laser energy source 28 at its proximal end. Once through this opening, laser energy is emitted from the fiber bundle as it is moved forwardly to form the channel in the myocardium and completely through the endocardium. After the channel has been formed, the distal end of the fiber bundle is retracted to a position within the end member of the device 16 which can then be moved to another location to repeat the procedure. When the end member of the device is removed, the relatively small opening in the epicardium substantially closes due to the tissue resiliency, thereby minimizing any blood flow from the channel just formed. The device is connected by a flexible line 36 to a vacuum source 37 which helps to remove debris caused by laser action during a channel forming procedure and also to initiate blood flow into each channel as it is formed in order to maximize the revascularization process.

As shown in FIG. 2, the device 16 comprises a housing 20 adapted to be hand held by the surgeon during an operative procedure, a J-shaped neck member 22 attached to the housing and an interchangeable distal head member 24 having a hollow piercing tip 25 (See FIG. 3A). An optical fiber bundle 26 whose proximal end is connected to the laser source 28 extends through the housing and through the neck member to the distal end member. Within the housing 20 the fiber bundle 26 is connected to a movable shuttle 30 (FIG. 3) which extends outside the housing and is connected to a thumb actuated control member 32. Thus, movement of the control member 32 by the surgeon will move the distal end 34 of the fiber bundle beyond the distal head member 24 of the neck member (FIG. 7). The vacuum line 36 extending from the vacuum source 37 such as a conventional hospital vacuum type canister device is connected to a barbed inlet 38 in the housing 20. This inlet communicates with an air passage 39 around the fiber bundle that extends to distal head member 24. Thus, when in use, a suction is provided at the distal head member 24 of the device 16 which performs two vital functions. First of all, the suction force draws the epicardium tissue firmly against the contacting face of the distal head member 24 so that a relatively small opening can be made in the epicardium muscle fibers to allow the distal end of the fiber bundle 26 to penetrate and engage the myocardium. As the fiber bundle is advanced by the surgeon beyond the epicardium opening and into the myocardium, laser pulses are produced from its distal end 34 to form a channel 18 through the myocardium. As the fiber bundle continues to advance, the air suction provided helps to remove debris caused by the laser and also draws blood into the channel to assure that the revascularization process will commence properly. When the fiber bundle is retracted after forming a channel, the distal end member 24 is moved away and the opening in the epicardium closes naturally with a minimum of bleeding. (FIG. 9)

Describing now the device 16 in greater detail, with reference to FIG. 3. The housing 20, which may be molded from a suitable plastic material, has an enlarged central cavity 40 to accommodate the shuttle 30. The latter has a cylindrical portion which surrounds and is firmly attached to the fiber bundle 26. Attached to the cylindrical portion is a web portion 42 which extends through an axial slot 44 in the housing. The web portion is connected to the control member 32 on the outside of the housing 20 which preferably has an arcuate configuration in cross section with a pair of external, transverse ridge portions 46 that facilitate easy thumb control by the surgeon.

Below the central cavity 40 is the barbed inlet 38 for the vacuum line 36 which communicates with the air passage 39 to the distal end member 24. An internal rubber disk 48 is provided within the housing to seal the air passage from the central cavity 40. The disk surrounds the fiber bundle and is held in place along its periphery by an annular groove 49.

At its forward end, the housing tapers to a threaded end portion 50 having a tapered end surface 52 for receiving a flared end 54 of the neck member 22. With the inner surface of this flared end in contact with the tapered end surface 52, a jam nut 56 around the neck member can be tightened on the threaded end portion 50 to secure the neck member to the housing 20. The jam nut 56 is preferably provided with a radially extending, integral fin or projection 57 which provides a means for easily turning the jam nut to loosen or tighten it. This enables the surgeon to quickly adjust the axial orientation of the J-shaped neck member 22 and thus the position of the distal head member 24 relative to the housing 20.

The proximal end of the optical fiber bundle 26 is connected to the source or generator 28 of laser energy which is preferably a Holmium laser that operates at a wave length in the range of 1.8 to 2.2 microns and a pulse frequency in the range of 2–25 Hertz. This type of laser is preferable because it provides high absorption efficiency, hemostosis and a moderate absorption range in myocardium tissue, and is compatible with optical fiber delivery.

At the laser generator, laser energy is supplied to the optical fiber bundle 26 which, at its distal end, has a diameter of around 1 mm. The optical fiber bundle is comprised of a plurality (e.g. 37) of glass fibers each having a diameter of 100 microns. These glass fibers are held together by a suitable plastic material, such a 353 ND Epoxy, and near its distal tip, the bundle is preferably surrounded by an annular tantalum marker which serves to retain the bundle in a closely packed geometric boundary surrounding the bundled fibers is a plastic protective sheath such as polypropelene having a wall thickness of 0.004 inches. Other fiber bundle configurations could be used within the scope of the invention.

In the embodiment shown, the neck member 22 of the device 16 is a tubular member having a uniform outside diameter (e.g. 0.120 inches) and inside diameter (e.g. 0.094 inches) preferably bent into an angular "J" shape within which the optical fiber bundle 26 is slidable. This neck portion is preferably made from a stainless steel which is heat treated to make it malleable and thus somewhat flexible. This enables the neck portion to be easily bent so that its distal end head member 24 can be positioned to accommodate the specific requirements of the surgical procedure being performed.

Removably attached to the distal end of the tubular neck is the enlarged positioning and stabilizing head member 24 for the device 16 which includes the hollow piercing tip 25 for making the initial opening in the epicardium. In the embodiment shown in FIGS. 4 to 9, this head member 24 has an annular flange portion with a generally planar end surface 27 that is transverse and preferably perpendicular to the axis of the inner passage and the fiber bundle 26 therein. One or more circular ridges 29 are provided in the end surface 27 so that the head member 24 will retain its position when pressed firmly against the epicardium of the heart.

The hollow tip member 25, preferably made of a suitable metal, e.g. stainless steel, has an inner diameter that is sufficient to accommodate the fiber bundle 26 with ample clearance so that the latter will slide freely through it. At its distal end the tip member is beveled to form a sharp anti-coring needle point 58. At its other end, the tip member has an enlarged tapered head portion 60.

The distal head member 24 has a body portion 62 with an enlarged central bore 64 having internal threads 66 that enables it to be quickly attached to the end of the neck member. In lieu of the threads 66, the head member 24 could be connected to the distal end of the neck member 22 by means of a Luer taper and lock nut combination (not shown) which is a standard connection system for tubular parts that is well known in the medical field.

Within one end of the bore 64 is an annular conical seat 68 which supports the enlarged head portion 60 of the tip member 25. A coiled spring 70 is preferably provided within the central bore to contact the enlarged head of the tip member and urge it against the seat 68. However, if a level of resistance is encountered by the tip member during its initial contact with the epicardium, the spring will allow some retraction of the tip member, thereby easing the initial penetration process.

An alternative form of head end member 24a according to the invention is shown in FIG. 3B. In this embodiment the removable piercing tip member 25 is protected by a movable outer sleeve member 72 that functions as a shield means and has a flared portion 74 with an end surface 76 that contacts the epicardium surface. The outer sleeve member is co-axial with and movable relative to an inner sleeve member 78 having an enlarged inner end portion 80. This inner sleeve has a central bore with internal threads 82 at its inner end to facilitate its connection with the distal end of the J-shaped neck member 22. Within the bore is an annular tapered surface 84 that forms a seat for the tapered head end of the piercing tip member 25. At the outer end of the inner sleeve member is an annular flange portion 86 which extends radially within an elongated inner slot 88 in the outer sleeve member 72. Similarly, at the inner end of the outer sleeve member is an inner end flange 90 that extends inwardly within an extended slot 92 that is formed by the end flanges 80 and 86 of the inner sleeve 78. Situated within the extended slot 92 is a coiled spring 94. When the head end member 24a is not in use and no axial force is applied against the end surface 76, the outer sleeve, 72, urged by the spring 94 extends beyond the end of the tip member 25 and thus protects it from any inadvertent contact with any surrounding object. When in use, as the end surface 76 of the outer sleeve is placed against the epicardium surface, it is moved rearwardly against the spring 94 so that tip member 25 can proceed to pierce the epicardium membrane in the desired manner.

The length of the tip member 25 is such that, in the embodiment of FIG. 3A, its tapered end normally extends around 0.2 inches beyond the contacting surface 27 of the head member 24. Similarly, in the embodiment of FIG. 3B, when the outer sleeve 72 is retracted against the spring 94, the tip member can project the same distance so that it will penetrate well through the epicardium in actual use. However, tip members of varying lengths may be used interchangeably by the surgeon to accommodate different conditions in accordance with the invention.

The use of the device 16 in a Transmyocardial Revascularization (TMR) procedure according to the invention is illustrated in FIG. 1 and in greater detail in FIGS. 6–9. After the surgeon makes an opening in the patient's chest to expose the left ventricle outer wall of the heart, the device 16, connected to its laser source is held by the surgeon.

During the TMR procedure the device 16 is maneuvered so that its head end 24 is placed against the epicardium of the left ventricle. (FIG. 6) The annular end face 27 of the head end member 24 serves as a stop as it is pressed against the outer surface of patient's heart. As this is done, the piercing tip member 25 first penetrates the tougher outer epicardium layer of the heart muscle while the distal end of the fiber bundle 26 is just inside the piercing member. The spring 70 provides a cushioning effect as the piercing member first engages the epicardium surface. With the head end member 24 in place and the piercing member 25 through the epicardium, the fiber bundle 26 is moved forward from the distal end of the device as shown in FIG. 7 by movement of the control knob 32 as laser pulses are simultaneously transmitted from its distal end 34. As laser energy is emitted, the distal end of the optical fiber bundle proceeds through the myocardium portion of the ventricle wall 12 and ultimately through the inner endocardium layer. (FIG. 8) As the fiber bundle advances and pulses laser energy it forms an expanding channel 18 in the myocardium that provides the revascularization of the heart muscle.

An important feature relative to the present invention is that the epicardium is pierced or penetrated mechanically but is not subjected to laser energy. The piercing tip member 25 penetrates through the epicardium with only a minimal damage to tissue and while protecting the distal end of the fiber bundle 26. Thus, after the channel 18 is fully formed, the fiber bundle 26 is retracted by the control knob 50 and the piercing member 25 is removed. (FIG. 9) The opening caused by the piercing member normally closes due to the resiliency of the muscle fibers in the epicardium so that there is no bleeding or only minimal bleeding on the outer surface of the heart.

From the forgoing it is apparent that the present invention provides an improved device for performing TMR procedures that affords versatility by virtue of its removable, replaceable distal tip members 25 and which enables the formation of effective channels for revascularization that will normally close at the epicardium membrane to minimize post-operative bleeding.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A hand-held transmyocardial revascularization (TMR) device for performing TMR on a patient's heart comprising:

a handle portion;

a tubular neck portion connected to the handle portion;

a head portion on a distal end of the tubular neck portion, the head portion forming a distal end contact surface for engaging the heart's epicardium;

an optical fiber having a proximal end configured for connecting to a laser energy source, the optical fiber extending through the handle portion and into the neck portion with a distal end of the optical fiber within the head portion;

adjustment means for moving the optical fiber within the handle portion, neck portion and head portion, the adjustment means is disposed on the handle portion; thereby enabling movement of the optical fiber's distal end beyond the head portion; and piercing means for: a) making an initial opening in the epicardium and b) allowing the optical fiber's movement therethrough when moved by the adjustment means, the piercing means is: i) axially movable relative to the head portion and ii) coupled to the head portion, whereby laser irradiation from the optical fiber's distal end forms a revascularizing channel in the heart's myocardium.

2. The device of claim 1 wherein the head portion includes at least one opening on the distal end contact surface, the at least one opening communicates through a tubular member extending through the handle portion, the tubular member is configured for connecting to a vacuum source, whereby activation of the vacuum source: a) draws the epicardium against the distal end contact surface, b) assists in ablated tissue removal and c) draws blood into the revascularizing channel.

3. The device of claim 1 wherein the head portion includes a substantially annular member having a flange portion forming the distal end contact surface, a body portion with a central bore and an opening in the flange portion, whereby the piercing means is retained in the central bore and the body portion can act as a safety shield member for the piercing means.

4. The device of claim 3 further including a cushioning member in the central bore of the head portion which engages the piercing means.

5. The device of claim 4 wherein the piercing means is a tubular piercing member that is axially biased by a spring and retractable into the body portion, the piercing member is extendable through the opening and has a tapered tip portion with an internal bore for slidable movement of the optical fiber within, whereby the cushioning member is the spring that engages and aligns with the tubular piercing member.

6. The device of claim 3 wherein the piercing means has an enlarged annular head member having a diameter greater than the flange portion's opening but less than the central bore.

7. The device of claim 3 wherein the piercing means is a tubular piercing member is extendable through the opening and having a tapered tip portion with an internal bore for slidable movement of the optical fiber within, the flange portion is an axially movable sleeve member that slides on the body portion, the flange portion is biased by a spring, the spring is disposed between a pair of retaining flange structures attached to the body portion and the flange portion, whereby the spring is a cushioning member.

8. The device of claim 7 wherein the tapered tip portion extends approximately 0.20 inches beyond the transverse face of the head portion.

9. The device of claim 3 wherein the head portion's flange portion defines a transverse face having at least one circular ridge member for positional stability.

10. The device of claim 1 wherein the piercing means extends approximately 0.20 inches beyond the contact surface of the head portion.

11. The device of claim 1 wherein the head portion including a means for attaching to the tubular neck portion thereby facilitating removal and replacement of the piercing means.

12. The device of claim 1 further including rotational adjusting means for radially orienting the neck portion relative to the handle portion.

13. The device of claim 12 wherein the rotational adjusting means is a jam nut disposed on the neck portion which threadedly attaches to the handle portion, the jam nut has a radial projection for ease of turning.

14. The device of claim 1 wherein the adjustment means includes within the handle portion an axial lumen, a movable shuttle within the axial lumen that is connected to the optical fiber, the optical fiber extends axially within the lumen, and a control knob attaches to the shuttle and extends outwardly from the handle portion, whereby the optical fiber can axially move within the handle portion by moving the control knob.

15. The device of claim 1 wherein the tubular neck portion has an offset curved shape at the neck portion's distal end and is made of a malleable material thereby allowing changes of the head portion's orientation relative to the handle portion.

16. A method of transmyocardial revascularization on a human heart, the method comprising the steps of:

a) providing a tubular piercing member whose distal end is a tapered tip with a means for cushioning the piercing member, the piercing member has a movable optical fiber disposed within the piercing member, the optical fiber's proximal end connects to a laser energy source;

b) forcing and cushioning the piercing member against a surface of the heart;

c) piercing the heart's surface while exerting axial force to the piercing member;

d) advancing the optical fiber's distal end beyond the tapered tip; and e) emitting laser energy from the distal end forming a revascularizing channel.

17. The method of claim 16 including a step of applying a suction force to the piercing member during step b).

18. The method of claim 16 including a step of applying a suction force to the piercing member during step e).

19. The method of claim 16 including steps following step e) of withdrawing the optical fiber while applying a suction force so as to draw blood into the revascularizing channel, thereby increasing myocardial revascularization and removal of ablated tissue.

20. The method of claim 16 wherein the step b) of cushioning the piercing member against the heart's surface is performed by the cushioning means that engages the tubular piercing member.

21. The method of claim 16 wherein in the step a) of providing a tubular piercing member, the tubular piercing member further includes a shielding means surrounding the piercing member for preventing injury to the surface of the heart prior to step b).

* * * * *